(12) United States Patent
Brown

(10) Patent No.: US 10,722,642 B2
(45) Date of Patent: Jul. 28, 2020

(54) INTEGRATED INTRAVENOUS (IV) CLAMP AND POWER SUPPLY

(71) Applicant: INTERNATIONAL BUSINESS MACHINES CORPORATION, Armonk, NY (US)

(72) Inventor: Kyle G. Brown, Apex, NC (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 16/432,145

(22) Filed: Jun. 5, 2019

(65) Prior Publication Data

US 2019/0282750 A1    Sep. 19, 2019

Related U.S. Application Data

(60) Division of application No. 16/142,782, filed on Sep. 26, 2018, now Pat. No. 10,391,236, which is a
(Continued)

(51) Int. Cl.
*F16M 11/22* (2006.01)
*F16M 11/42* (2006.01)
(Continued)

(52) U.S. Cl.
CPC .......... *A61M 5/1418* (2013.01); *A61B 50/26* (2016.02); *A61M 5/1415* (2013.01); *A61M 5/1417* (2013.01); *F16B 2/065* (2013.01); *F16M 11/42* (2013.01); *H02M 7/04* (2013.01); *A61B 50/13* (2016.02); *A61M 5/14* (2013.01); *A61M 2205/82* (2013.01); *A61M 2205/8256* (2013.01)

(58) Field of Classification Search
CPC ........ F16M 11/22; F16M 11/42; H01R 13/72; H01R 33/945; A61M 5/1415; A61M 5/1418; A61B 50/23
USPC ....... 361/826, 111; 248/129, 176.1; 439/501, 439/577; 211/60.1; 206/564
See application file for complete search history.

(56) References Cited

U.S. PATENT DOCUMENTS 3,651,803 A * 3/1972 Bimler ............... A61B 17/6408
602/16
5,083,741 A * 1/1992 Sancoff ............... A61M 39/284
24/17 B
(Continued)

OTHER PUBLICATIONS

List of IBM Patents on Patent Applications Treated as Related; (Appendix P), filed Jun. 5, 2019; 2 pages.

*Primary Examiner* — Xiaoliang Chen
(74) *Attorney, Agent, or Firm* — Cantor Colburn LLP; Michael O'Keefe

(57) ABSTRACT

An intravenous (IV) pole assembly includes a non-conductive support element, distribution rails respectively disposed along a length of the non-conductive support element and a clamping element. The distribution rails are respectively configured for power distribution along the length of the non-conductive support element. The clamping element includes a hinged clamp, which is attachable to the non-conductive support element at an attachment point defined along the length of the non-conductive support element, and a connector by which power is selectively transmittable from the distribution rails to a powered device supportable on the hinged clamp.

8 Claims, 6 Drawing Sheets

Related U.S. Application Data continuation of application No. 14/874,898, filed on Oct. 5, 2015, now Pat. No. 10,112,004.

(51) Int. Cl.
   *H01R 33/945* (2006.01)
   *H01R 13/72* (2006.01)
   *A61M 5/14* (2006.01)
   *A61B 50/26* (2016.01)
   *F16B 2/06* (2006.01)
   *H02M 7/04* (2006.01)
   *A61B 50/13* (2016.01)

(56) References Cited

U.S. PATENT DOCUMENTS

| | | | |
|---|---|---|---|
| 5,401,256 A * | 3/1995 | Stone | A61M 39/287 251/10 |
| 5,482,239 A * | 1/1996 | Smith | A61G 5/10 248/229.13 |
| 5,588,166 A * | 12/1996 | Burnett | A61G 7/05 248/214 |
| 6,445,571 B1 | 9/2002 | Inniss et al. | |
| 6,790,059 B2 | 9/2004 | Poehlau | |
| 7,777,995 B2 | 8/2010 | Malkus et al. | |
| 7,874,410 B2 | 1/2011 | Fulbrook et al. | |
| 8,292,656 B2 | 10/2012 | Mydlarz | |
| 8,500,465 B1 | 8/2013 | Ross et al. | |
| 8,585,419 B2 | 11/2013 | Byrne | |
| 8,879,241 B2 | 11/2014 | Lu et al. | |
| 8,902,569 B1 | 12/2014 | Wishman et al. | |
| 8,964,359 B2 | 2/2015 | Bauer et al. | |
| 8,994,213 B1 | 3/2015 | Czamara et al. | |
| 9,122,466 B1 * | 9/2015 | Kellett | G06F 1/26 |
| 10,112,004 B2 | 10/2018 | Brown | |
| 2005/0006538 A1 * | 1/2005 | Turi | A61M 5/1415 248/188.1 |
| 2007/0159772 A1 | 7/2007 | Morice | |
| 2007/0257164 A1 * | 11/2007 | Wells | G09F 15/00 248/125.2 |
| 2008/0116157 A1 * | 5/2008 | Fulbrook | A61M 5/1415 211/60.1 |
| 2008/0217495 A1 * | 9/2008 | Roepke | A47K 17/00 248/223.41 |
| 2009/0301927 A1 * | 12/2009 | Fvlbrook | A61B 90/57 206/564 |
| 2010/0081318 A1 | 4/2010 | Mydlarz | |
| 2013/0187011 A1 * | 7/2013 | Rifenburg | A61G 12/008 248/68.1 |
| 2013/0238795 A1 | 9/2013 | Geffin et al. | |
| 2014/0035365 A1 | 2/2014 | Jeffrey | |
| 2014/0361129 A1 | 12/2014 | Gomez et al. | |
| 2015/0202106 A1 * | 7/2015 | Hight | A61G 13/04 602/36 |
| 2015/0256665 A1 | 9/2015 | Pera et al. | |
| 2017/0095608 A1 | 4/2017 | Brown | |
| 2019/0022304 A1 | 1/2019 | Brown | |

\* cited by examiner

INTEGRATED INTRAVENOUS (IV) CLAMP AND POWER SUPPLY

CROSS-REFERENCE TO RELATED APPLICATIONS

This application is a divisional application of U.S. application Ser. No. 16/142,782, titled "INTEGRATED INTRAVENOUS (IV) CLAMP AND POWER SUPPLY", and filed on Sep. 26, 2018, which is a continuation of U.S. application Ser. No. 14/874,898, titled "INTEGRATED INTRAVENOUS (IV) CLAMP AND POWER SUPPLY", and filed on Oct. 5, 2015 having U.S. Pat. No. 10,112,004. The entire contents of U.S. application Ser. Nos. 16/142,782 and 14/874,898 are incorporated herein by reference.

BACKGROUND

The present invention relates to intravenous (IV) poles and, more particularly, to an IV poles with an integrated clamp and power supply.

IV poles are used in the medical industry to suspend bags of fluid for introduction into a patient through an IV line. The current IV pole design was originally developed in the 1940's when patients had an average of two different IV bags attached to them. However, with advances in medical technology, the average patient can have far higher numbers of IV features attached to them. In some cases, such as intensive care units (ICUs) of hospitals, a given patient can have nine or ten IV features attached to him/her. Meanwhile, due to further advances, IV gravity feeds have been replaced by infusion pumps, which are computer-controlled pumps that control the flow rate and amount of fluids being introduced into the patient along each IV line.

A problem faced by health care professionals, such as hospital nurses, is that even on the most modern IV poles, power is supplied to the individual features (i.e., pumps) through conventional 110V outlets. This leads to a profusion of different alternative current (AC) lines and transformers being plugged into a limited number of power outlets and thus necessitates the use of power strips. This is not only a dangerous situation, since plugs can accidentally slip out of their outlet, leading to drains on the built-in backup batteries in the IV pumps, but the multiplication of cords leads to lost time in critical situations when a patient must be moved. Indeed, during patient movement, cords for the pumps all have to be located, untangled and disconnected from their respective outlets, carefully wrapped to avoid having anyone step on them or to avoid losing them, and then reinserted into new AC outlets in the new patient location.

The time required for this process can be significant when a patient has several different IV lines and presents unnecessary danger when patient movement must be done as quickly as possible.

SUMMARY

According to an embodiment of the present invention, an intravenous (IV) pole assembly is provided and includes a non-conductive support element, distribution rails respectively disposed along a length of the non-conductive support element and a clamping element. The distribution rails are respectively configured for power distribution along the length of the non-conductive support element. The clamping element includes a hinged clamp, which is attachable to the non-conductive support element at an attachment point defined along the length of the non-conductive support element, and a connector by which power is selectively transmittable from the distribution rails to a powered device supportable on the hinged clamp.

According to another embodiment, an intravenous (IV) device transportation apparatus is provided and includes an IV device, which is operable when supplied with direct current (DC), a non-conductive support element that includes a movable base portion and an upper portion extending from the base portion, a power converter disposed in the base portion, distribution rails respectively electrically coupled to the power converter and disposed along a length of the upper portion and a clamping element. The clamping element includes a hinged clamp, on which the IV device is supportable and which is attachable to the non-conductive support element at an attachment point defined along the length of the upper portion and a connector by which DC is selectively transmittable to the IV device from the power converter via the distribution rails.

According to another embodiment, a method of transporting an intravenous (IV) device transportation apparatus is provided. The method includes clamping a hinged clamp, on which IV devices are supported, to a non-conductive support element, converting alternating current (AC) into direct current (DC) for operating the IV devices in the non-conductive support element and distributing and selectively transmitting DC from the power converter to the IV devices along the non-conductive support element.

According to another embodiment, an intravenous (IV) device transportation apparatus power system is provided. The system includes a floor that in turn includes embedded power distribution elements. The system further includes an IV device, which is operable when supplied with power, a non-conductive support element that includes a base portion, which is movable along the floor, and an upper portion extending from the base portion, a receiver disposed in the base portion to be receptive of power from the power distribution elements, distribution rails respectively electrically coupled to the receiver and disposed along a length of the upper portion and a clamping element. The clamping element includes a hinged clamp, which is attachable to the non-conductive support element at an attachment point defined along the length of the non-conductive support element, and a connector by which power is selectively transmittable to the IV device from the receiver via the distribution rails.

According to yet another embodiment, a method of operating an intravenous (IV) device transportation apparatus power system is provided. The method includes clamping a hinged clamp, on which IV devices are supported, to a non-conductive support element, embedding power distribution elements in a floor, receiving power for operating the IV devices in the non-conductive support element and distributing and selectively transmitting the received power to the IV devices along the non-conductive support element.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
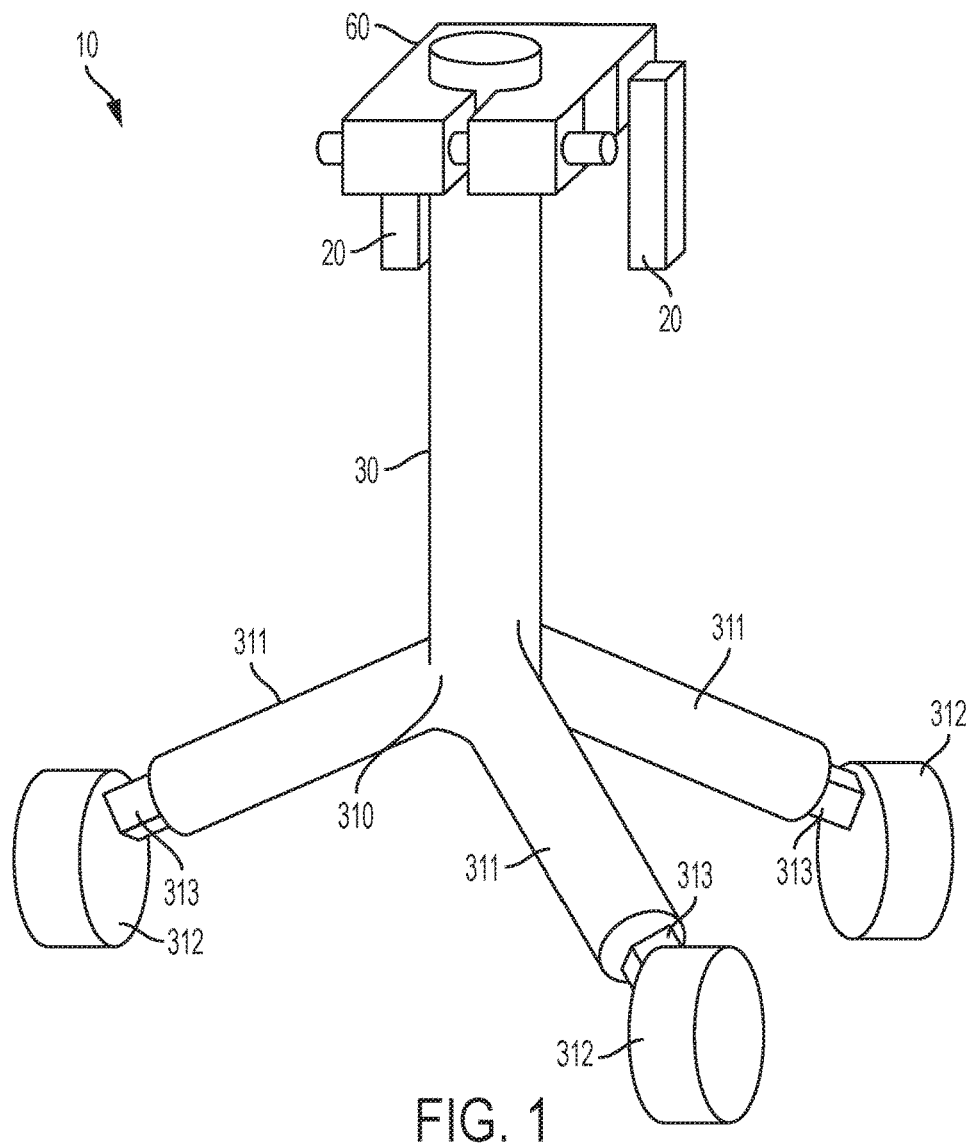
FIG. 1 is a perspective view of an intravenous (IV) device transportation apparatus in accordance with embodiments.
Figure 2:
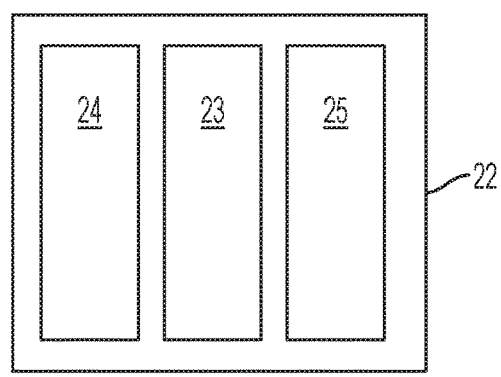
FIG. 2 is a schematic illustration of an IV device supportable on the IV device transportation apparatus of FIG. 1.

Pumps on intravenous (IV) poles generally operate using direct current (DC) power and include a DC power outlet. As will be described below, multiple aspects of IV pump design are combined with centralized alternating current (AC) to DC power conversion and DC power distribution to thereby eliminate a need for AC/DC conversion at individual endpoints. This in turn eliminates redundancy, reduces overall power consumption and also greatly reduces heat generation and noise, all of which are desirable advantages in a hospital situation.

As a particular result of the combination, an IV pole is provided that includes an integrated AC/DC power converter, a DC power distribution "strip" that runs through and along the center of the IV pole and a clamp that can slide up and down the IV pole. When the clamp is attached and tightened to the IV pole, the clamp can secure a particular IV pump to the IV pole at a particular vertical location and can securely contact the DC power distribution network within the IV pole by way of a DC connector (e.g., of a standard 2.5 mm type) that can plug into the IV pump. As will be explained, the clamp, plug and pump can be removed from the IV pole with one operation as a single, integrated unit, and then by reattached to another IV pole in a single set of motions. This greatly reduces the time it takes to move IV pumps from one IV pole to another and also reduces the amount of clutter and the number of operations that a nurse or other healthcare professional must perform in order to shift IV pumps from one IV pole to another IV pole.

With reference to FIGS. 1-8, an IV device transportation apparatus 10 is provided and will be referred to hereinafter as an "IV device transportation apparatus 10" or simply as an "apparatus 10." The apparatus 10 includes one or more IV devices 20, which are each operable when supplied with DC power, a non-conductive support element 30, a power converter 40 (see FIG. 4), distribution rails 50 (see FIG. 5) and a clamping element 60 (see FIGS. 5-8). The IV device 20 may be any electrical IV device including, but not limited to, an IV pump and a monitor.

The IV device 20 may have a body 22 that is supportable by the clamping element 60, a control portion 23 by which the IV device 20 is controllable by an operator, an operable portion 24 and a local power source 25. The operable portion 24 is formed to execute pumping operations in the case of the IV device 20 being the IV pump or monitoring operations in the case of the IV device 20 being the monitor. The local power source 25 may be provided as a replaceable or rechargeable battery that can be used to continually power the IV device 20 when power is unavailable from the power converter 40 and the distribution rails 50.

Figure 3:
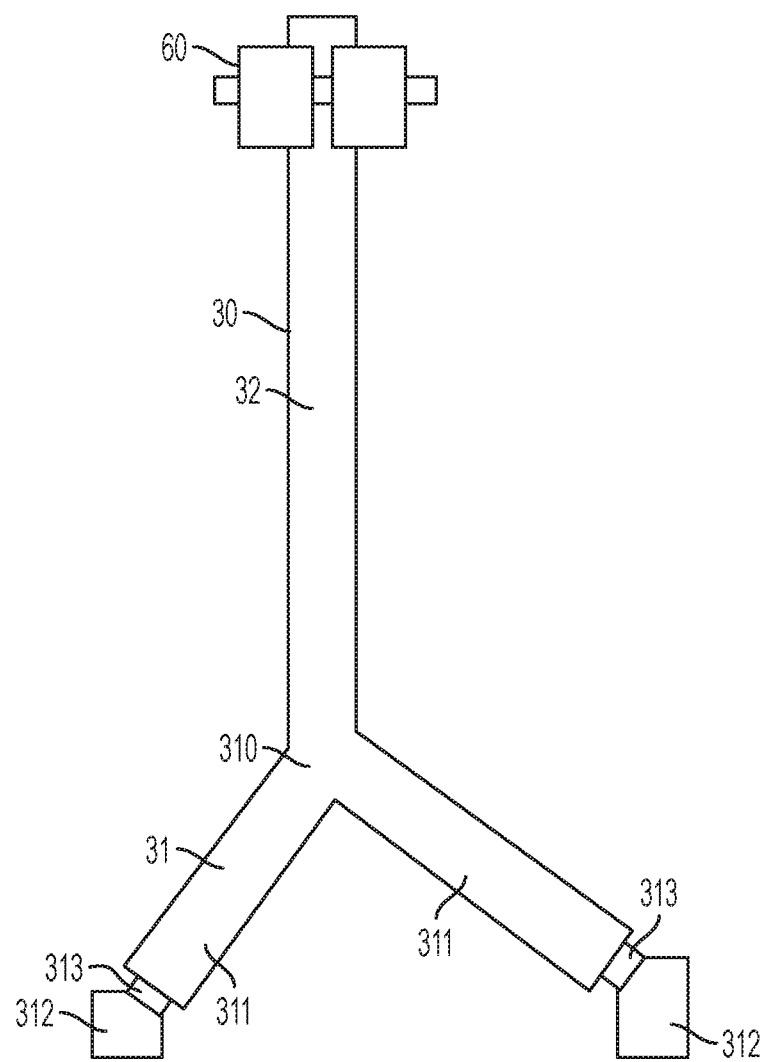
FIG. 3 is a side view of a non-conductive support element in accordance with embodiments.
Figure 4:
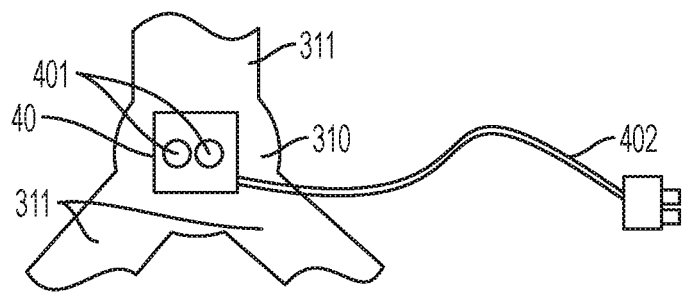
FIG. 4 is a cross-sectional view of a movable base member of the non-conductive support element of FIG. 3.
Figure 5:
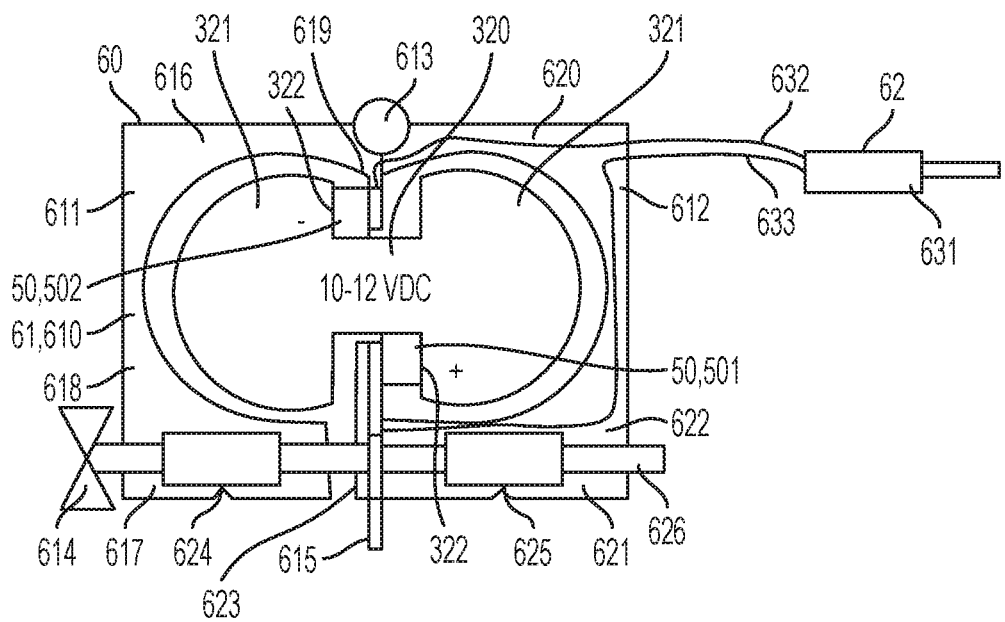
FIG. 5 is a cross sectional view of a clamping element and an upper portion of the non-conductive support element of FIG. 3.

With reference to FIGS. 3-5, the non-conductive support element 30 includes a movable base portion 31 and an upper portion 32. The movable base portion 31 may be provided in multiple configurations that offer stable support for the upper portion 32 and which allow for mobility of the apparatus 10 as a whole. In accordance with one embodiment, the movable base portion 31 may be provided as a tripod with a central hub 310, three legs 311 extending outwardly and downwardly from the central hub 310, three wheel elements 312 respectively disposed at distal ends of the three legs 311 and three couplings 313 by which each of the wheel elements 312 are coupled to a corresponding one of the legs 311. As shown in FIG. 4, the three legs 311 may be generally, uniformly angled with respect to each other and may have similar respective lengths as measured from the central hub 310.

The upper portion 32 extends upwardly from the central hub 310 of the movable base portion 31 and is configured to provide support for at least one or more IV devices 20. Thus, particularly, in the case where multiple IV devices 20 are supported on the upper portion 32, the upper portion 32 should be configured to permit an evenly weighted arrangement of the at least one or more IV devices 20 to avoid risks of the apparatus 10 toppling over. In any case, dimensions of the movable base portion 31 may also be variable to decrease such toppling risks. That is, the legs 311 may be extending radially outwardly by a sufficient amount such that a center of gravity of the apparatus 10 remains within a predefined range even when multiple IV devices 20 are supported on one side of the upper portion 32. Moreover, in accordance with further embodiments, the wheel elements 312 can be tightened or otherwise configured to provide resistance to certain types of de-stabilizing movements, for example.

In general, the upper portion 32 may include a central, electrically non-conductive member 320 (hereinafter referred to as a "central member 320") and first and second lateral, electrically non-conductive members 321 (hereinafter referred to as "lateral members 321"). In accordance with embodiments and, as shown in FIGS. 3 and 5, the central member 320 has an elongate body with a generally polygonal cross-sectional shape and the lateral members 321 may be provided on either lateral side of the central member 320 and may have semi-hemispherical cross-sectional shapes. In accordance with further embodiments the lateral members 321 may be integrally connected to the lateral sides of the central member 320 such that the lateral members 321 define oppositely facing shoulder surfaces 322, which are adjacent to the central member 320. The distribution rails 50 may be respectively supportable on the shoulder surfaces 322.

With continued reference to FIGS. 3 and 4, the power converter 40 is generally disposed in the movable base portion 31 and, in accordance with embodiments, may be disposed in the central hub 310. The power converter 40 may be provided as an AC to DC transformer 400 and includes first leads 401 and second leads 402. The first leads electrically couple the transformer 400 to each of the distribution rails 50 and the second leads may be provided as a single wire and plug that is connectable to a wall outlet, such as a standard 110 or 220 volt AC outlet. Thus, when the transformer 400 is plugged in and electrically coupled to the distribution rails 50, the distribution rails 50 carry DC current along their respective lengths in a closed circuit in series with the transformer 400.

The distribution rails 50 may include a first distribution rail 501 and a second distribution rail 502. The first distribution rail 501 includes an electrically conductive strip that serves as a positive DC current line and extends along a length of the upper portion 32 from one of the first leads 401 of the power converter 40. The second distribution rail 502 similarly includes an electrically conductive strip that serves as a negative DC current line and extends along the length of the upper portion 32 toward the other of the first leads 401. In accordance with embodiments and, as shown in FIG. 4, the first distribution rail 501 has a rectangular cross-sectional shape and is supported on the shoulder surface 322 of one of the lateral members 321 and the proximal portion of the near side of the central member 320 and the second distribution rail 502 has a rectangular cross-sectional shape and is supported on the shoulder surface 322 of the other of the lateral members 321 and the proximal portion of the near side of the central member 320.

The clamping element 60 includes a hinged clamp 61 and a connector 62. The hinged clamp 61 may be provided with a clamshell structure 610 that is configured to be tightened onto and thus attached to the non-conductive support element 30 at an attachment point, which is defined along any portion of the length of the non-conductive support element 30. The connector 62 is configured to be selectively actuated such that DC power is selectively transmittable to the corresponding IV device 20 from the power converter 40 via the distribution rails 50.

Figure 6:
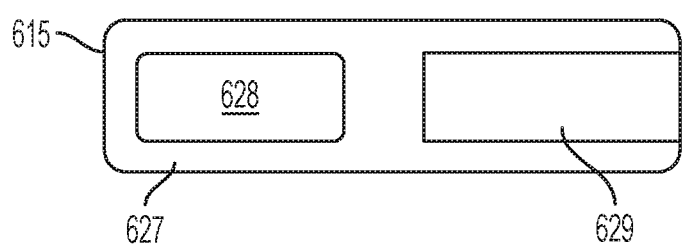
FIG. 6 is a side schematic illustration of a plunger of the clamping element of FIG. 5 in accordance with embodiments.
Figure 7:
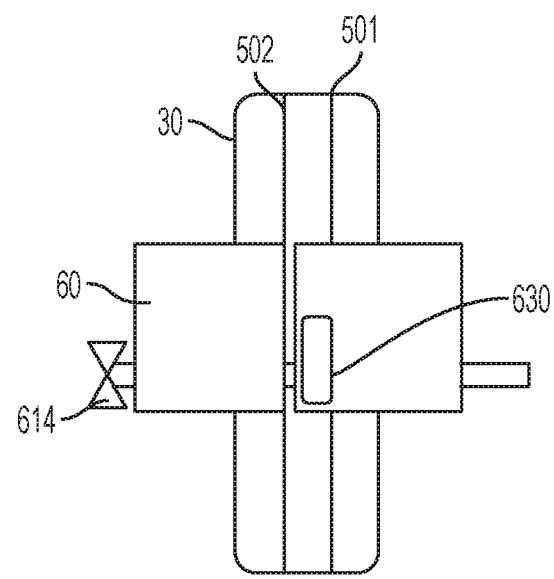
FIG. 7 is a rear-side view of the clamping element of FIG. 5 in accordance with embodiments.
Figure 8:
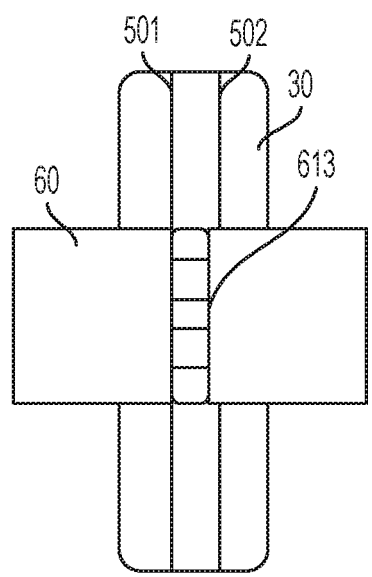
FIG. 8 is a front-side view of the clamping element of FIG. 5 in accordance with embodiments.

With continued reference to FIG. 5 and with additional reference to FIGS. 6-8, the clamshell structure 610 of the hinged clamp 61 may include first and second clamshell portions 611 and 612, a hinge 613 (see FIG. 8) by which the first and second clamshell portions 61 and 612 are pivotably coupled to one another, a fastening element 614 and a plunger 615. The first and second clamshell portions 611 and 612 each have an exterior surface of variable shape and a concave interior surface that is configured to fit around the lateral members 321 at first and second sides of the non-conductive support element 30, respectively.

In accordance with embodiments and, as shown in FIG. 5, the first clamshell portion 611 may include a first end 616 to which the hinge 613 is coupled, a second end 617, a body 618 integrally interposed between the first and second ends 616 and 617 and a first flange 619. The body 618 includes the concave interior surface that fits around the corresponding one of the lateral members 321 and may be separated from the corresponding one of the lateral members 321 at a variable distance. In accordance with further embodiments, the second clamshell portion 612 may include a first end 620 to which the hinge 613 is coupled, a second end 621, a body 622 integrally interposed between the first and second ends 620 and 621 and a second flange 623. The body 622 includes the concave interior surface that fits around the corresponding one of the lateral members 321 and may be separated from the corresponding one of the lateral members 321 at a variable distance. The first flange 619 extends radially inwardly from a distal edge of the first end 616 toward the second distribution rail 502 and the second flange 623 extends radially inwardly from a distal ends of the second end 621 toward the first distribution rail 501.

The fastening element 614 may be configured to draw the first and second clamshell portions 611 and 612 toward one another about the hinge 613 in a tightening direction relative to the first and second sides of the non-conductive support element 30. To this end, the fastening element 614 may include first threaded portion 624, second threaded portion 625 and screw element 626. The first threaded portion 624 has interior threading and resides in the second end 617 of the first clamshell portion 611 and the second threaded portion 625 has interior threading and resides in the second end 621 of the second clamshell portion 612. The screw element 626 has exterior threading and is insertible through the second ends 617 and 621 to threadably engage with the first and second threaded portions 624 and 625.

During an assembly operation of the apparatus 10, an IV device 20 may be supportively attached to the hinged clamp 61 and the hinged clamp 61 may be slid up and down the non-conductive support element 30 to any location. Once the hinged clamp 61 is disposed at a desired location, the screw second element 626 can be inserted into the second ends 617 and 621 and rotated in a tightening direction to clamp the hinged clamp 61 in place at the location. During a disassembly operation, the screw element 626 is rotated in a loosening direction in order to release the hinged clamp 61 and the IV device 20 from the desired location on the non-conductive support element 30.

As shown in FIGS. 5, 6 and 7, the plunger 615 is configured to selectively electrically couple the connector 62 to at least one of the distribution rails 50 (e.g., to the first distribution rail 501) and may include a body 627, which is formed to define a through-hole 628 through which the screw element 626 is extendable, and a conductive element 629 that wraps around an end of the body 627. The plunger 615 is extendable through a through-hole 630 (see FIG. 7) defined in the second end 621 of the second clamshell portion 612 proximate to and substantially in parallel with the second flange 623 such that the conductive element 629 faces the first distribution rail 501. Thus, once the hinged clamp 61 is tightened onto the non-conductive support element 30 at the desired location, the plunger 615 can be selectively pushed by an operator in a radially inward direction toward the first distribution rail 501 until the conductive element 629 makes electrical contact with the first distribution rail 501.

In accordance with embodiments, it is to be understood that the plunger 615 may be spring-loaded and lockable. In such cases, the spring-loading of the plunger 615 will normally bias the plunger 615 away from an electrical contact location whereby a user must overcome the bias in order to push the plunger 615 toward the first distribution rail 501. A locking mechanism would then maintain the plunger 615 in place at least until the plunger 615 is selectively withdrawn or the hinged clamp 61 is loosened and released from the non-conductive support element 30.

As shown in FIG. 5, the connector 62 may include a plug 631, which is insertible into the IV device 20, wiring lines 632, 633. The wiring lines 632, 633 are configured to be electrically coupled to the distribution rails 50. In accordance with embodiments, wiring line 632 may run through the first ends 616 and 620 of the first and second clamshell portions 611 and 612 to make contact with the second distribution rail 502 and wiring line 633 may run through the second end 621 of the second clamshell portion 612. This wiring line 633 will then make electrical contact with the conductive element 629 such that, when the plunger 615 is pushed toward the first distribution rail 501, the conductive element 629 electrically couples the wiring line 633 to the first distribution rail 501.

Figure 9:
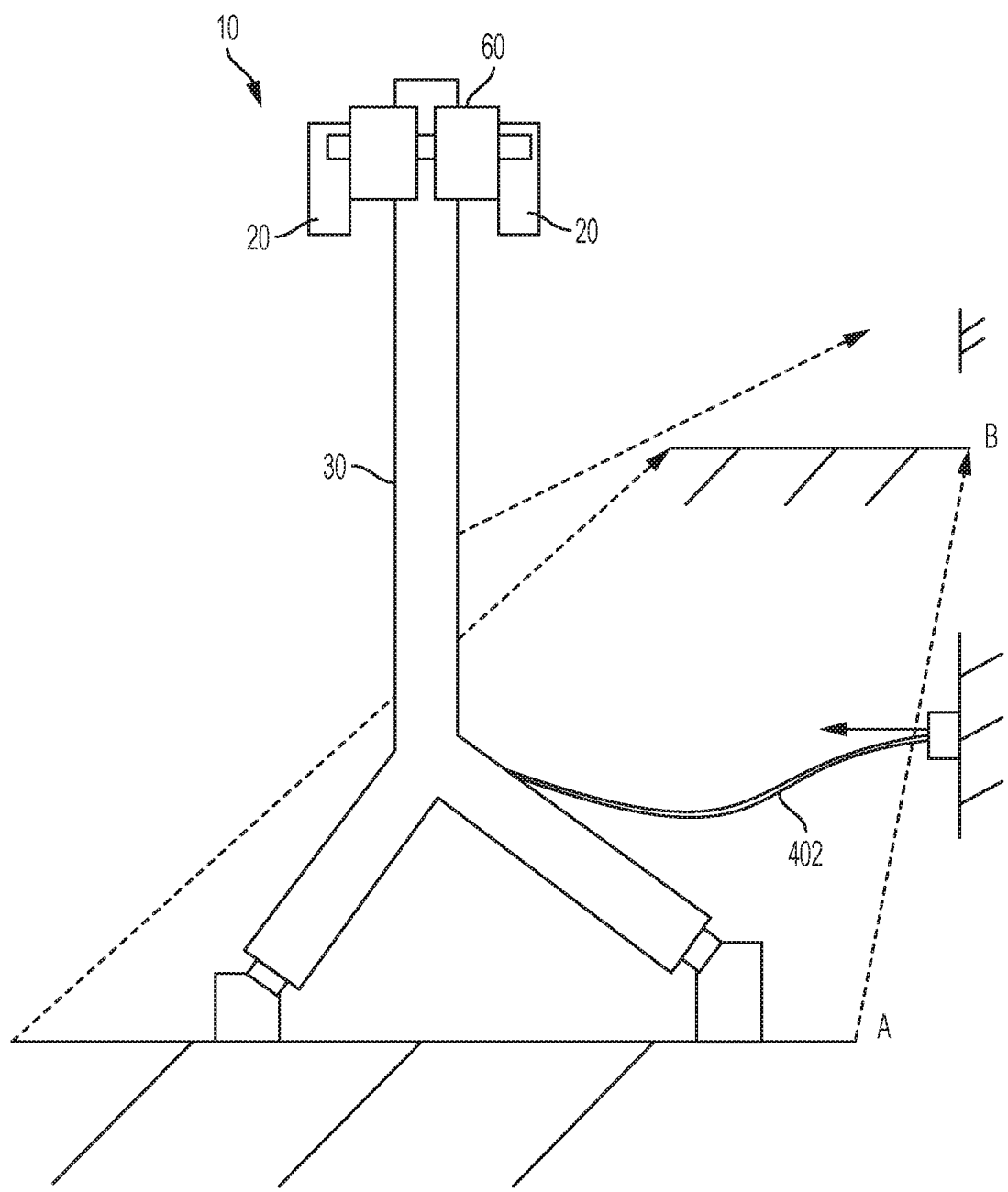
FIG. 9 is a not-to-scale, slightly perspective illustration of an IV device transportation apparatus in use in accordance with embodiments.

With reference to FIG. 9, the apparatus 10 may be provided in a hospital, for example, to permit multiple IV devices 20 to receive power in the form of DC from the above-described distribution rails 50 with the apparatus 10 as a whole including only a single plug by which current is transmitted to the distribution rails 50 via the power converter 40. As such, should the apparatus 10 need to be moved from location A (in the foreground of FIG. 9) to location B (in the background of FIG. 9), the operator need only remove the single plug from its outlet before initiating the movement and is only required to plug in the single plug at the destination. Thus, movement of the apparatus 10 is easy and can be executed with minimal time spent with the IV devices 20 un-powered or battery-powered.

Figure 10:
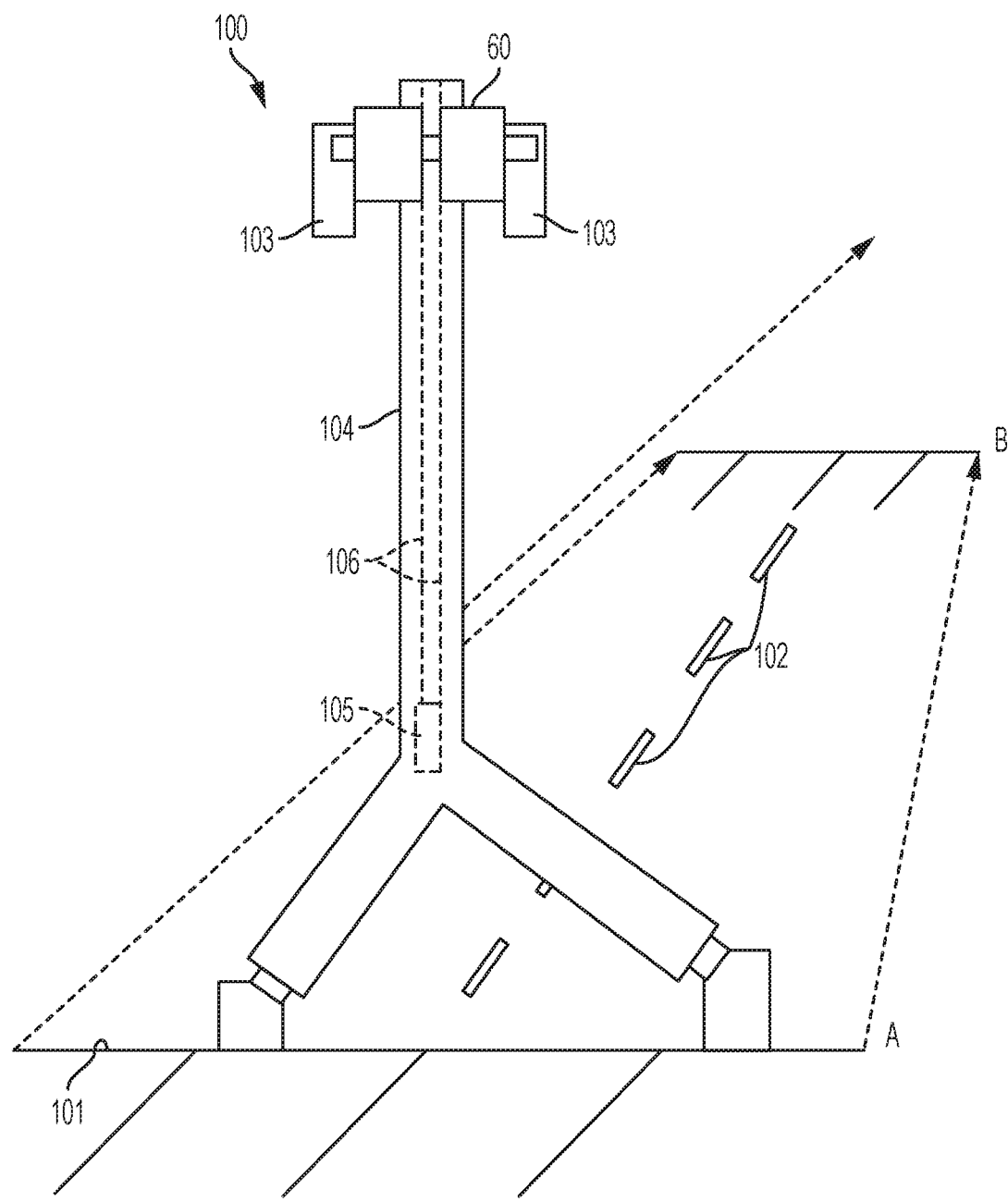
FIG. 10 is a not-to-scale, slightly perspective illustration of an IV device transportation apparatus power system in accordance with embodiments.

With reference to FIG. 10, an IV device transportation apparatus power system 100 (hereinafter referred to as a "power system 100") is provided and includes features that are similar to those described above and different from those described above. In the former case, further detailed descriptions of similar features will not be necessary with the following description relating only to the different features.

As shown in FIG. 10, the power system 100 includes a floor 101, which in turn includes embedded power distribution elements 102, one or more IV devices 103 that are operable when supplied with power, a non-conductive support element 104 similar to the non-conductive support element 30, a receiver 105, distribution rails 106, and a clamping element 107 that is similar to the clamping element 60. The embedded power distribution elements 102 may include, for example, radio frequency (RF) transmitters by which electrical power is transmittable over a certain range of distances. The receiver 105 is disposed in the base portion of the non-conductive support element 104 to be receptive of power from the power distribution elements 102 and the distribution rails 106 are respectively electrically coupled to the receiver 105 and disposed along a length of the upper portion non-conductive support element 104.

In accordance with embodiments, the embedded power distribution elements 102 are arranged in the floor 101 such that, as the base portion of the non-conductive support element 104 is moved along the floor 101 within a predefined track, the receiver 105 remains within range of at least one of the embedded power distribution elements 102. Thus, the power system 100 is configured to provide power for the IV devices 103 as the non-conductive support element 104 is moved from location A (in the foreground of FIG. 10) to location B (in the background of FIG. 10) even if the non-conductive support element 104 is not plugged into a wall outlet at either location.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An intravenous (IV) device transportation apparatus, comprising:
   an IV device, which is operable when supplied with direct current (DC);
   a non-conductive support element comprising a movable base portion and an upper portion extending from the base portion;
   a power converter disposed in the base portion;
   distribution rails respectively electrically coupled to the power converter and disposed along a length of the upper portion; and
   a clamping element comprising:
   a hinged clamp, on which the IV device is supportable and which is attachable to the non-conductive support element at an attachment point defined along the length of the upper portion; and
   a connector by which DC is selectively transmittable to the IV device from the power converter via the distribution rails.

2. The IV device transportation apparatus according to claim 1, wherein the movable base portion comprises wheeled supports and the upper portion comprises:
   a central, non-conductive member; and
   first and second lateral, non-conductive members, which are semi-hemispherical and supportive of the distribution rails.

3. The IV device transportation apparatus according to claim 1, wherein the power converter comprises an alternating current (AC) to DC transformer.

4. The IV device transportation apparatus according to claim 1, wherein the distribution rails respectively comprise electrically conductive strips.

5. The IV device transportation apparatus according to claim 1, wherein the hinged clamp comprises a clamshell structure configured to be tightened onto the non-conductive support element.

6. The IV device transportation apparatus according to claim 1, wherein the hinged clamp comprises:
   first and second clamshell portions configured to fit around first and second sides of the non-conductive support element, respectively;
   a hinge by which the first and second clamshell portions are pivotably coupled; and
   a fastening element configured to draw the first and second clamshell portions toward one another in a tightening direction relative to the first and second sides of the non-conductive support element.

7. The IV device transportation apparatus according to claim 1, wherein the hinged clamp comprises a plunger configured to selectively electrically couple the connector to at least one of the distribution rails.

8. The IV device transportation apparatus according to claim 1, wherein the connector comprises:
   a plug, which is insertible into the powered device; and
   wiring lines, which are configured to be electrically coupled to the distribution rails.

* * * * *